United States Patent [19]

Brighton

[11] Patent Number: 4,535,239
[45] Date of Patent: Aug. 13, 1985

[54] METHOD AND APPARATUS FOR REMOTE MEASUREMENT OF A PARTICULATE MATTER ON A MOVING SHEET

[75] Inventor: Andrew P. Brighton, Muncie, Ind.

[73] Assignee: Ball Corporation, Muncie, Ind.

[21] Appl. No.: 500,675

[22] Filed: Jun. 3, 1983

[51] Int. Cl.$^3$ .............................................. G01J 1/00
[52] U.S. Cl. .................................... 250/339; 250/340
[58] Field of Search ................... 250/339, 340, 358.1, 250/359.1, 571, 572; 356/446, 448

[56] References Cited

U.S. PATENT DOCUMENTS

| | | | |
|---|---|---|---|
| 3,807,868 | 4/1974 | Simila | 356/448 |
| 3,870,884 | 3/1975 | Williams | 250/359.1 |
| 4,165,939 | 8/1979 | Woodrow et al. | 250/572 |
| 4,306,151 | 12/1981 | Chase | 250/359.1 |
| 4,421,983 | 12/1983 | Fogle et al. | 250/339 |

*Primary Examiner*—Alfred E. Smith
*Assistant Examiner*—Richard Hanig
*Attorney, Agent, or Firm*—Gilbert E. Alberding

[57] ABSTRACT

Method and apparatus are disclosed for detecting and measuring the quantity of particulate matter on a substrate without contacting the sheet or disturbing the particulate matter. Directed, non-visible light energy interacts with particulate matter on the surface of the sheet; and a portion of such incident light energy is redirected at an acute angle that is significantly different from the angle of reflection of such light energy by the surface of the sheet. Infrared energy, particularly that having a wave length of about 940 nanometers, is particularly effective in the detection and measurement of clear epoxy powder; and the portion of such infrared energy effected by the particulate material may be related to the quantity of particulate material on the substrate. In the system for effecting the method and apparatus, a detector generates a voltage signal that may be related to the weight of coating material on the surface of the sheet by the relationship:

$$W_p = \log_{10}^{-1} \frac{(V_R - k_1)}{k_2},$$

where
  W is the density of coating material on one surface of the substrate,
  $V_R$ is the level of the amplified voltage signal, and
  $k_1$ and $k_2$ are constants of the system.

7 Claims, 4 Drawing Figures

METHOD AND APPARATUS FOR REMOTE MEASUREMENT OF A PARTICULATE MATTER ON A MOVING SHEET

BACKGROUND OF THE INVENTION

This invention relates to a method and apparatus to detect and measure the quantity of particulate matter on a substrate, and more particularly to determine the quantity of powdered coating material on the surface of a moving metallic sheet without contacting the sheet or disturbing the coating.

Strips used to make metal containers and container ends for such beverages as beer, carbonated soft drinks, and the like are given coatings of resinous polymeric materials to form coherent, uniform, and functional coatings as thin as 0.05 mils in thickness. Such coatings can be formed from powdered coating materials, such as thermosetting epoxy powders, having average particle sizes in the range of from 1 to 15 microns, and preferably having an average particle size less than 10 microns. In applying such coatings, a preferable method is by the electrostatic deposition of such powdered coating materials. Among the advantages of the preferred electrostatic deposition method are efficiency in the use of the coating materials and the ability to achieve uniformity in very thin coatings. It is important, however, in such thin coatings that the requisite amount of powder necessary to provide a coherent protective coating on the substrate be present; thus, it is desirable that the presence and quantity of particulate material on the substrate be detected and measured in order to avoid the production of unusable sheet. This problem is particularly difficult in the commercial manufacture of such metallic sheet where it is coated as it is moved through a deposition zone at rates up to several hundred feet per minute. Any effort to contact the sheet will disturb the coating by dislodgement of particulate matter.

SUMMARY OF THE INVENTION

This invention solves these problems and provides a method and apparatus for detecting and measuring the quantity of particulate matter on a substrate without contacting the sheet or disturbing the particulate matter. The invention employs directed, non-visible light energy and the discovery that the particulate matter on the surface of the sheet will interact with such incident light energy and redirect a portion of such incident light energy at an acute angle that is significantly different from the angle of reflection of such light by the surface of the sheet. It has further been discovered that infrared energy, particularly that having a wave length of about 940 nanometers, is particularly effective in such detection and measurement and that a portion of such infrared energy effected by the particulate material may be related to the quantity of particulate material on the substrate.

In the preferred method of this invention, non-visible energy, such as infrared energy having a wave length of 940 nanometers, is directed at the surface of the moving sheet so that it impinges on the sheet at an angle of about 45°. The portion of such incident energy leaving the sheet along a line that is normal to the moving sheet at the zone of impingement is detected. This detected signal may be converted to a voltage level and amplified and processed with other signals to provide a result that can be interpolated by an anti-log generator to develop a signal proportionate to the weight of particulate material.

The system for practicing the invention preferably includes a source of infrared energy having a wave length of about 940 nanometers and a detector of infrared energy sensitive to wave lengths of about 940 nanometers. The infrared energy source is supported so that its infrared energy impinges upon the moving sheet at an angle of about 45° and the detector is supported so that its energy-receiving surface faces the moving sheet on a line passing through the zone of impingement of the infrared energy and lying normal to the sheet. The output of the detector may be amplified to provide a voltage signal logarithmically related to the coating weight and from which the coating weight may be derived by the relationship:

$$W_p = \log_{10}^{-1} \frac{(V_R - k_1)}{k_2},$$

where
W is the coating weight in milligrams per square inch per side,
$V_R$ is voltage level in volts,
$k_1$ and $k_2$ are constants expressed as voltage signals.

Other features of the invention will be apparent from the following drawings and detailed description.

DETAILED DESCRIPTION OF THE PREFERRED EMBODIMENTS

Figure 1:
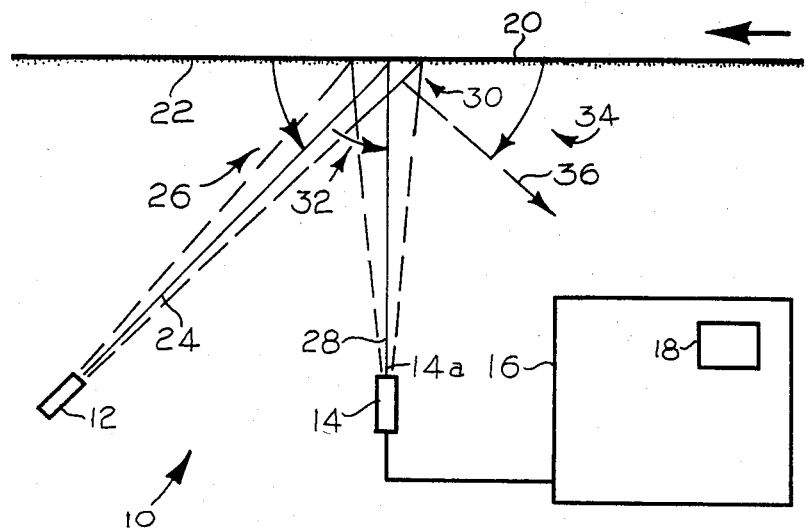
FIG. 1 is a diagrammatic illustration of a system of this invention.

FIG. 1 illustrates a typical system 10 which may be used to practice this invention. This system includes a source 12 of non-visible energy, a detector 14 sensitive to the non-visible energy emanating from source 12, and a means 16 for processing the signal from the detector 14 to provide at an indicator 18 an indication of particulate matter present on sheet 20, which is moving from right to left as shown in FIG. 1.

The energy source 12, which is preferably a source of infrared energy having a wave length 940 nanometers, is positioned by a support (not shown) so that it directs its energy at the coated surface 22 along a line 24 lying at an angle 26 of about 45°.

The detector 14 has a portion of its surface 14a adapted to receive energy, and the detector 14 is adapted to generate a voltage signal that corresponds to the amount of energy received at surface 14a. The detector 14 is positioned in the system so that its energy-receiving surface 14a may accept energy in the direction of a line 28 that is normal to the surface 22 of the moving sheet 20 and that passes through the zone of impingement 30 of the energy source 12 on the coated surface 22.

It has been discovered that where the surface of a substrate 20 is coated with particulate matter, a portion of the energy from such a source 12 will be affected by the particulate matter in such a manner that a significant portion is redirected through an acute angle 32 that is substantially different from the angle of reflection 34 of the energy from the surface 22 of the moving sheet. That is, as shown in FIG. 1, a portion of the energy reaching the zone of impingement 30 will be directed along line 28 where it may be detected by a detector 14. Energy reflected from the surface of sheet 20, however, will be reflected along an angle of reflection 34, which is equal to the angle of incidence 26, that is, along the phantom line 36. Thus, a signal proportional to the presence of particulate matter on the surface of sheet 20 is detected along the line 28 in a direction normal to the surface of the sheet and not along the angle of reflection of the light energy.

In the application of this invention to the manufacture of aluminum strip for can manufacture, it has been found that infrared energy having a wave length of 940 nanometers is particularly desirable where the particulate matter deposited on the surface of the sheet comprises a clear (i.e., water-like) epoxy resin having an average particle size less than 10 microns. The use of such energy, which does not lie in the visible range and is not present in any significant quantities in ambient light and other energies generally present in the industrial environments in which such coating material is prepared, permits a system that may be uniformly applied in industry relatively independently of varying conditions from location to location. The source 12 can be a Skan-A-Matic Model No. L33107, and the detector 14 can be a Skan-A-Matic Model No. P33101 for such an emitter. The detector provides low output for bare metal and the output of the detector increases logarithmically with increasing thickness of particulate matter on the aluminum surface when the emitter and detector are arranged as shown in FIG. 1.

Figure 3:
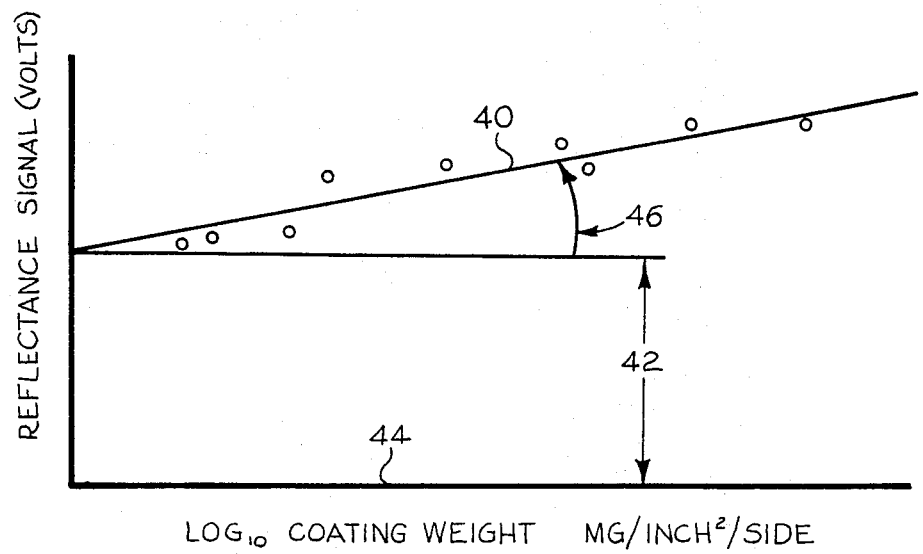
FIG. 3 is a graph showing the relationship between the voltage signal and coating weight of a typical system of the invention.

Data typical of such systems is shown, for example, in FIG. 3. The relationship between coating weight and the amplified signal from a detector is thus related by the relationship $$W_p = \log_{10}^{-1} \frac{(V_R - k_1)}{k_2},$$

Where
- $W_p$ is the density of particulate material on the surface of the substrate in units of weight divided by units of area, for example, grams per inch$^2$ per side,
- $V_R$ is the amplified voltage of the detector 14,
- $k_1$ is a constant corresponding to the displacement 42 of the line 40 from the axis 44 of FIG. 3; and
- $k_2$ is a constant corresponding to the angle 46 of the line 40 with respect to axis 42.

Figure 2:
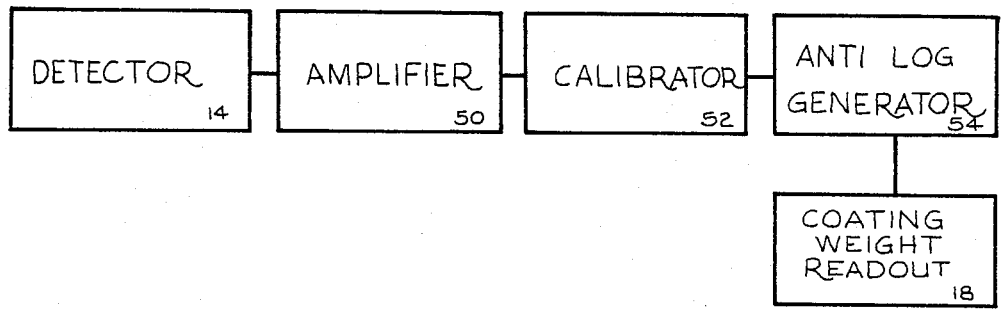
FIG. 2 is a block diagram of the means used to determine and measure the coating material present on the substrate.
Figure 4:
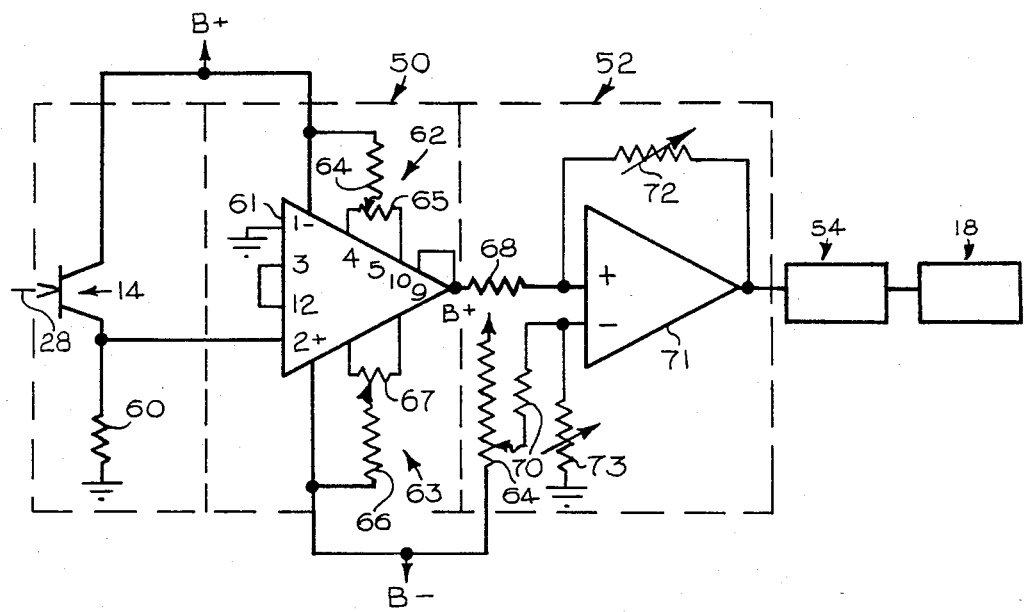
FIG. 4 is a diagram of a typical circuit to develop a signal corresponding to coating weight.

FIG. 2 is a block diagram of the means to detect and indicate the coating material present on the substrate. The system includes the detector 14, amplifier 50, a calibrator 52, and anti-log generator 54, and an indicator 18. As indicated above, the detector can be a Scan-A-Matic infrared detector, Model No. P33101. The circuits comprising the amplifier 50, calibrator 52, and anti-log generator 54 are shown in FIG. 4. The indicator 18 may be a light or alarm signal or, in the preferred embodiment, may be a digital readout or a voltage meter calibrated, for example, in milligrams per square inch.

Referring now to FIG. 4, the detector 14, which may be a Scan-A-Matic Model P33101 is connected from a voltage source to ground through a resistance 60. Where the Scan-A-Matic P33101 detector is used, it may be connected to 15 volts positive and to a resistance 60 of, typically, 100 ohms.

Energy reaching the detector 14 along line 28 (see FIG. 1) produces a signal in resistor 60 which is coupled to amplifier 50. Amplifier 50 includes an operational amplifier 61 which may be an Analog Device No. AD524 device or an equivalent instrument amplifier. The amplifier is connected between positive and negative voltage sources. For an Analog Device No. AD524 device, the sources may be plus and minus 15 volts. The amplifier may be provided with an input offset nulling circuit 62 and an output offset nulling circuit 63 with the amplifier gain set to 100. The input nulling circuit, for example, includes resistors 64 and 65 appropriately connected between the positive voltage source and the amplifier terminals. The output nulling circuit 63 includes, for example, resistor 66 and 67 connected between the negative voltage source and the appropriate terminals of amplifier 61. For use in a preferred circuit with an Analog Device No. AD524, resistances 64 and 66 may be, for example, 10,000 ohms and resistances 65 and 67 may be 10,000 ohms potentiometers having the resistors 64 and 66 connected to their slider.

The output of amplifier 50 is coupled to the calibrator circuit 52. The output of amplifier 61 is coupled to a resistance 68 to provide $V_R$ input to the calibrator amplifier 71. The calibrator 52 includes potentiometer 69 connected between the voltages to which amplifier 61 is connected; and in the preferred circuit, this is plus and minus 15 volts. A resistance 70 is connected between the slider of potentiometer 69 and amplifier 71. The operational amplifier 71 is used to develop the calibrating signals.

This calibration amplifier may be a National Semiconductors LM107 device or its equivalent. The input signal from amplifier 50 representing $V_R$ is connected to the positive input of the operational amplifier and is provided with feedback from the output of the calibrating amplifier 71 through variable resistance 72. A variable resistance 73 is connected between ground and the connection between the resistive input 70 to the calibrating amplifier from potentiometer 69. In the preferred calibrator circuit 54, resistances 68 and 70 are 300,000 ohms. Potentiometer 69 which is connected between plus and minus 15 volts is a 50,000 ohm potentiometer; and variable resistances 72 and 73 have a 200,000 ohm maximum value.

In the operation of calibrator 52, the output from potentimeter 69 is adjusted to provide a constant voltage signal corresponding to $k_1$ (the constant corresponding to the displacement 42 of line 40 from axis 44 of FIG. 3). The relationship of the resistances of resistor 72 and resistor 68 calibrate the signal corresponding to $k_2$ (a constant corresponding to the angle 46 of line 40 with respect to axis 42 of FIG. 3), where the values of the resistances 68 and 70 are equal and the value of resistances 72 and 73 are adjusted to be equal. The potentiometer 72 and 73 may be ganged to provide for simple adjustment.

The calibrated signal from calibrator 52 is coupled to an anti-log generator which may be an Intersil No. ICL8049 device or its equivalent; and the output of the anti-log generator 54 drives a display 18 which may analog or digital and calibrated in units of milligrams per square inch per side.

While I have shown a preferred embodiment of my invention, other embodiments may be devised without departing from the spirit and scope of the following claims.

I claim:

1. A method of measuring the particulate coating material on a substrate, comprising:
   directing infrared energy having a wave length of about 940 nanometers at a substrate at an angle of about 45°,
   detecting infrared energy from the particulate material along a line that is normal to the substrate and lying at an angle at 45° from the direction from the incident infrared energy,
   generating a voltage from the detected infrared energy,
   amplifying the voltage signal to provide a voltage level from which coating weight can be derived by the relationship $$W_p = \log_{10}^{-1} \frac{(V_R - k_1)}{k_2},$$

where
   $W_p$ is the density of coating material on one surface of the substrate,
   $V_R$ is the level of the amplified voltage signal, and
   $k_1$ and $k_2$ are constants of the system.

2. A non-contact system for measuring particulate matter on a moving sheet, comprising:
   a source of infrared energy having a wave length of about 940 nanometers,
   a detector for infrared energy sensitive to wave lengths of about 940 nanometers,
   means to support the source so that its infrared energy impinges upon the moving sheet at an angle of about 45°,
   means to support the detector so its energy-receiving surface lies in a line normal to the moving sheet passing through the zone of impingement of infrared energy, and
   means to provide an output from the detector to indicate the quantity of particulate material on the sheet.

3. In a method of detecting the quantity of particulate matter on a moving sheet, the improvement comprising:
   directing non-visible energy having wavelength of about 940 nanometers at the surface of the moving sheet so that it impinges on the sheet at an angle of about 45° and detecting the infrared energy from the moving sheet along a line normal to and passing through the zone of impingement of energy on the surface of the sheet.

4. A method of detecting a quantity of particulate matter having a particle size less than about 10 microns on the surface of a moving metallic sheet without contacting the sheet, comprising:
   directing infrared energy having a wave length of about 940 nanometers at the surface of the metallic sheet with an acute angle of incidence, and detecting the infrared energy having a wave length of about 940 nanometers leaving the surface of the sheet along a line lying normal to the metallic surface end and at an acute angle with respect to the directed infrared energy in a direction differing substantially from the direction of reflection of the incident infrared energy from the metallic surface to detect particulate matter on said surface.

5. In the method of claim 4 wherein the angle of incidence of infrared energy is about 45° and the infrared energy from the particulate matter is detected in a direction normal to the metallic surface of the sheet.

6. A system for measuring particulate material on the surface of a moving sheet without contacting the surface, comprising:
   a source of infrared energy adapted to provide an interaction with the particulate material on the surface of the sheet,
   a detector sensitive to said infrared energy,
   a support for said source to direct the infrared energy at the surface of the sheet at an acute angle,
   a second support for the detector to direct its energy-receiving surface at the surface of the sheet along a line removed from the direction of the source by an acute angle and from the direction of reflection of the energy from the surface of the sheet,
   an amplifier for the signal from the detector,
   a calibrator for the signal,
   an anti-log interpolator for the calibrated signal, and
   an indicator for the output of the anti-log interpolation.

7. In a method of detecting the quantity of particulate matter on a moving sheet, the improvement comprising:
   directing infrared energy having a wavelength of about 940 nanometers at the surface of the moving sheet so that it impinges on the sheet at an angle of about 45°;
   detecting the infrared energy from the moving sheet along a line normal to and passing through the zone of impingement of energy on the surface of the sheet;
   converting said detected signal to an amplified voltage level signal;
   subtracting a constant voltage level from the amplified voltage level signal;
   dividing the difference by a constant; and interpolating the result by an anti-log generator to develop a signal proportionate to the weight of particulate matter.

* * * * *